United States Patent [19]

Kakimoto et al.

[11] Patent Number: 4,844,911
[45] Date of Patent: Jul. 4, 1989

[54] QUALITY IMPROVEMENT OF ALCOHOLIC LIQUORS

[75] Inventors: Shigeya Kakimoto, Kawanishi; Yasuhiro Sumino, Kobe; Hideaki Yamada, Kyoto; Satoshi Imayasu, Kyoto; Eiji Ichikawa, Kyoto; Tetsuyoshi Suizu, Kyoto, all of Japan

[73] Assignees: Takeda Chemical Industries, Osaka; Gekkeikan Sake Company, Ltd., Kyoto, both of Japan

[21] Appl. No.: 108,201

[22] Filed: Oct. 14, 1987

[30] Foreign Application Priority Data

Oct. 14, 1986 [JP] Japan .................................. 244893
Jun. 12, 1987 [JP] Japan ............................... 62-147512
Jul. 17, 1987 [JP] Japan ............................... 62-179738

[51] Int. Cl.$^4$ .................. C12C 11/00; C12G 1/00; C12G 3/00; C12H 1/00
[52] U.S. Cl. ...................................... 426/11; 426/12; 426/15; 426/16; 426/29; 426/61; 426/592
[58] Field of Search ...................... 426/11, 12, 15, 16, 426/28, 29, 49, 51, 52, 61–63, 592

[56] References Cited

FOREIGN PATENT DOCUMENTS 56-20830 5/1981 Japan .
52-90698 1/1986 Japan .

OTHER PUBLICATIONS

Takamatsu "Chemical Abstracts" 82, col. 15260b (1975).
Suzuki et al., "Applied and Environmental Microbiology", pp. 379–382 (Mar. 1979).

*Primary Examiner*—Marianne Cintins
*Attorney, Agent, or Firm*—Wenderoth, Lind & Ponack

[57] ABSTRACT

Alcoholic liquors containing carbamide are treated with the urease which has the optimal pH for the activity in an acid region, especially in the region of pH2 to 5. By such treatment, the carbamide can be completely decomposed and removed from the alcoholic liquors in a much smaller amount of urease and in a short time as compared with a conventional treatment according to a urease having the optimal pH in the neutral to alkaline region. This method is more advantageous from the viewpoint of practical use and the quality of the thus obtained alcoholic liquors are superior to that obtained by the conventional treatment.

5 Claims, No Drawings

QUALITY IMPROVEMENT OF ALCOHOLIC LIQUORS

This invention relates to method of improvement of quality of alcoholic liquors.

All brewages including refined sake, beer, wine, and samshu, and the final mash, the material before distillation into whisky, brandy, shochu, etc. contain carbamide (urea), which is the main cause of deterioration of alcoholic liquors, giving off-flavor to alcoholic liquors and deteriorating the flavor of alcoholic liquors when they are pasteurized or stored for a long period. For removal of carbamide, is known a method wherein urease enzyme preparation is added to alcoholic liquors or to the final mash and allowed to react at a low temperature of 10°-20° C. (Official Gazette of Japanese Patent No. 20830/1981).

Urease (E.C.3.5.1.5.) is an enzyme which decomposes carbamide into ammonia and carbon dioxide gas, and is distributed widely in nature, e.g. in plants, animals, and microorganisms. Conventionally urease from *Canavalia Adans.* and urease from *Bacillus pasteuri* have been produced industrially for practical use.

The urease products described above have the optimal pH in the neutral to alkaline region, and at a pH in the acidic region not only the reaction is very difficult to proceed, but also the enzyme is apt to be deactivated, particularly remarkably when the reaction temperature is above room temperature or when the reaction is conducted in a reaction mixture containing organic solvents such as alcohols. Therefore, for example the disclosed in the Official Gazette of Japanese Patent No.20830/1981 has defects that a very large amount of urease derived from *Canavalia Adans.* or from bacteria (optimal pH 6-8) is required to be added to remove carbamide present in refined sake containing about 20% of alcohol, and that the reaction can proceed only at a low temperature of 10°-20° C. over a long time; thus the method is not necessarily satisfactory for alcoholic liquors manufacture from the industrial viewpoint.

The inventors felt acutely the necessity of a urease preparation which is stable and acts well even in acidic alcoholic liquors containing alcohol in order to produce alcoholic liquors of high quality, and as the result of their research, they found that treatment with urease derived from lactic acid bacteria having an optimal pH in the acidic region pH 2-5 can remove by decomposing carbamide present in alcoholic liquors with a small amount of urease in a very short time even at a higher temperature; after further studies, the inventors have completed this invention.

That is, this invention relates to improvement of quality of alcoholic liquors characterized by treatment of alcoholic liquors with acid urease.

The acidic urease used in this invention means the one which produces 2 moles of ammonia and 1 mole of carbon dioxide gas from 1 mole of carbamide and 1 mole of water, the optimal pH for the activity being in the region of pH 2-5, preferably pH 2-4.5, and there is no limitation with respect to the general properties of the enzyme, such as pH stability, optimal temperature, thermostability, substrate specificity, nature of inhibitors, Km value, and molecular weight.

Acid urease is usually produced by culture of acid urease-producing bacterial strains. Such strains are preferably those of so-called "lactic acid bacteria", for example those belonging to genera of Streptococcus, Pediococcus, Leuconostoc, Lactobacillus and Bifidobacterium. Representatively *Streptococcus faecium, Streptococcus mitis, Lactobacillus casei var. casei, Streptococcus mitior, Streptococcus bovis, Lactobacillus fermentum, Bifidobacterium infantis, Bifidobacterium suis* and *Bifidobacterium choerinum* are preferably used, but there is no limitation with respect to the strain; even new isolates from milk products, soil, rancid and souring putrefacted food, organs and excretes from animals, etc. may be used as far as they can produce acid urease. In addition, variants obtained artificially from the strains by UV irradiation or by treatment with mutagens, and other bacterial strains obtained by recombination of the artificially separated gene fragments necessary for expression of the said acid urease activity may be used.

Acid urease-producing strains include, in the concrete, *Lactobacillus fermentum* JCM 5867 (IFO 14511, FERM P-8990), *Lactobacillus fermentum* JCM 5868 (IFO 14512, FERM P-8991), *Lactobacillus fermentum* JCM 5869 (IFO 14513, FERM P-8992), *Streptococcus mitior* PG-154 (IFO 14633, FERM P-9460), *Streptococcus bovis* PG-186 (IFO 14634, FERM P-9461) and *Bifidobacterium choerinum* PG-196 (IFO 14635, FERM P-9462). The IFO numbers mean the accession numbers in Institute for Fermentation, Osaka (IFO) and the FERM P numbers mean the accession numbers in Fermentation Research Institute, Agency of Industrial Science and Technology, Ministry of International Trade and Industry (FRI).

These microorganisms, which were deposited at FRI on the date of the following Table, have been converted to a deposit under the Budapest Treaty and stored at FRI under the accession numbers of FERM BP as shown in the following Table.

| Microorganism | Date of deposit at FRI | Accession Number under the Budapest Treaty |
|---|---|---|
| Lactobacillus fermentum JCM 5867 | October 4, 1986 | FERM BP-1454 |
| Lactobacillus fermentum JCM 5868 | October 4, 1986 | FERM BP-1445 |
| Lactobacillus fermentum JCM 5869 | October 4, 1986 | FERM BP-1446 |
| Streptococcus mitior PG-154 | July 7, 1987 | FERM BP-1448 |
| Streptococcus bovis PG-186 | July 7, 1987 | FERM BP-1449 |
| Bifidobacterium choerinum PG-196 | July 7, 1987 | FERM BP-1450 |

*Lactobacillus fermentum* JCM 5867, *Lactobacillus fermentum* JCM 5868 and *Lactobacillus fermentum* JCM 5869 are listed on "Research Communication No. 13 (Annual Report 1985-1986), 1987" published by IFO under the above identified IFO Nos.

The six microorganisms described above have the following bacteriological properties.

| Properties | Strains | | |
|---|---|---|---|
| | JCM 5867 | JCM 5868 | JCM 5869 |
| shape of cells | short rod (0.6–1.2 × 1.0–2.0)μ | short rod (0.6–1.2 × 1.0–2.0)μ | short rod (0.6–1.2 × 1.0–1.2)μ |
| motility | − | − | − |
| sporulation | − | − | − |
| Gram stain | + | + | + |
| optimal growth | 30–40° C. | 30–40° C. | 30–40° C. |

|  | -continued | | |
|---|---|---|---|
| temperature growth at 45° C. | + | + | + |
| growth at 15° C. | − | − | − |
| oxygen demand | facultative anaerobe | facultative anaerobe | facultative anaerobe |
| oxidation-fermentation test | fermented | fermented | fermented |
| fermentation type | DL-lactic acid and ethanol produced abundantly from glucose | DL-lactic acid and ethanol produced abundantly from glucose | DL-lactic acid and ethanol produced abundantly from glucose |
| gas formation | | | |
| glucose | + | + | + |
| gluconic acid | + | + | + |
| acid formation | | | |
| glucose | + | + | + |
| gluconic acid | + | + | + |
| mannitol | − | − | − |
| salicin | − | − | − |
| raffinose | + | + | + |
| dulcitol | − | − | − |
| inositol | − | − | − |
| lactose | + | + | + |
| melezitose | − | − | − |
| melibiose | + | + | + |
| maltose | + | + | + |
| cellobiose | − | − | − |
| esculin | − | − | − |
| glycerol | − | − | − |
| mannose | − | − | − |
| rhamnose | − | − | − |
| ribose | + | + | + |
| arabinose | − | − | − |
| sorbitol | − | − | − |
| sucrose | + | + | + |
| fructose | + | − | − |
| galactose | + | + | + |
| trehalose | − | − | − |
| xylose | − | − | − |
| catalase | − | − | − |
| oxidase | − | − | − |
| nitrate reduction | − | − | − |
| gelatin liquefaction | − | − | − |
| auxotrophy | thiamine, calcium pantothenate, niacin, | thiamine, calcium pantothenate, niacin, | thiamine calcium pantothenate, niacin, riboflavine |

| | Strains | | |
|---|---|---|---|
| Properties | PG-196 | PG-154 | PG-186 |
| origin | pig intestinum duodenum | pig intestinum jejunum | pig colon |
| shape of cells | short rod (0.6–0.8 × 1.0–1.5)μ | coccus (0.8–1.0 × 0.8–1.0)μ | coccus (0.8–1.0 × 0.8–1.0)μ |
| motility | − | − | − |
| sporulation | − | − | − |
| Gram stain | + | + | + |
| oxygen demand | microaerophile | facultative anaerobe | facultative anaerobe |
| oxidation-fermentation test | fermentative | fermentative | fermentative |
| fermentation type | homo L-lactic acid | homo L-lactic acid | homo L-lactic acid |
| catalase | − | − | − |
| oxydase | − | − | − |
| nitrogen reduction | − | − | − |
| gelatin liquefaction | − | − | − |
| hydrolysis of starch | + | − | +(weakly) |
| decomposition of esculin | + | − | − |
| MR test | +(weakly) | + | + |
| VP test | − | +(weakly) | +(weakly) |
| formation of indol | − | − | − |
| formation of hydrogen sulfide | − | ND | ND |
| NH₃ formation from arginine | − | − | − |
| litomus milk | − | − | − |
| gas formation from glucose | − | − | − |
| optimal growth temperature (°C.) | 25–37 | 30–37 | 25–37 |
| growth at 45° C. | − | − | − |
| growth at 15° C. | − | − | − |
| growth at pH 4.0 | − | − | − |
| growth at pH 9.6 | − | − | − |
| growth in 3% aqueous sodium chloride solution | + | − | − |
| growth in 6.5% aqueous sodium chloride solution | − | − | − |
| α-hemolysis | − | − | +(weakly) |
| β-hemolysis | − | − | − |
| acid formation | | | |
| adonitol | − | ND | ND |
| arabinose | + | − | − |
| arabitol | − | ND | ND |
| arbutin | − | +(weakly) | + |
| cellobiose | + | + | + |
| dulcitol | − | ND | ND |
| fructose | − | + | + |
| galactose | + | + | + |
| gluconate | − | − | − |
| glucose | + | + | + |
| glycerol | − | − | − |
| inositol | − | − | − |
| inulin | − | − | − |
| lactose | + | + | + |
| maltose | + | + | + |
| mannitol | − | − | − |
| mannose | − | − | + |
| melezitose | − | − | − |
| melibiose | + | − | − |
| α-methyl-glucoside | +(weakly) | ND | ND |
| raffinose | + | + | − |
| rhamnose | − | − | − |
| ribose | +(weakly) | − | − |
| salicin | − | + | + |
| sorbitol | − | − | − |
| sorbose | − | ND | ND |
| starch | + | − | + |
| sucrose | +(weakly) | + | + |
| trehalose | − | − | − |
| xylose | + | − | − |
| xylitol | − | ND | ND |
| content of DNA (%) | 65.5 | 40.3 | 40.1 |
| type of peptideglycan | Lys | ND | ND |
| | Orn | | |
| | Ser | | |
| | Ala | | |
| | Glu | | |

In the above Table, the symbol "ND" means that experiments are not carried out, and Lys, Asp, Ala, Glu, Orn, Ser and m-DAP represent lysine, aspartic acid, alanine, glutamic acid, ornithine, serine and mesodiaminopimeric acid, respectively. The taxonomical position of the above strains was examined by comparing the above bacteriological properties with the description of Bergey's Manual of Systematic Bacteriology, Vol.2 (1986). As the results, it is appropriate that PG-196 strain, though each acid formation from arabinose, cellobiose, ribose and xylose is positive, is a microorganism of *Bifidobacterium choerinum;* PG-154 strain, though α-hemolysis is negative, is that of *Streptococcus*

*mitior;* and PG-186 strain, though hydrolysis of esculin is negative, is that of *Streptococcus bovis.*

Acid urease is produced from these strains continuously or intermittently by conventional standing culture, shaking culture, aeration-spinner culture, or solid culture. The culture media used are those of conventional composition wherein the bacteria can grow. The carbon sources are appropriately selected from carbohydrates, fat, fatty acid, and alcohols which can be assimilated and are used separately or in combination. The nitrogen sources include organic nitrogen sources such as peptone, soybean flour, cotton seed flour, corn steep liquor, yeast extract, meat extract, malt extract, and whey, and inorganic nitrogen sources such as ammonium sulfate, ammonium chloride, ammonium nitrate and ammonium phosphate, which are used separately or in appropriate combination according to the necessity. It is desirable that, in addition to the carbon sources and nitrogen sources, essential growth factors or growth promotors such as minerals, amino acids and vitamins are added to the media. Carbamide, thiourea or the like is sometimes added to induce the production of acid urease. For the control of pH and foam during culture, it is effective to supplement appropriately caustic alkali solution, sodium carbonate solution, or calcium salt solution, or an antifoaming agent.

Temperature of cultivation is selected from the range suitable for growth of the bacteria used, being usually 15° C. to 50° C., preferably 25° C. to 40° C. Cultivation is continued for a time sufficient for growth of the bacteria and for production of acid urease, usually for 5 to 50 hours.

After cultivation under the conditions described above, acid urease is usually contained in the bacterial cells. The viable cells collected from the culture by centrifugation, sedimentation, aggregation, filtration through porous membrane or ceramics, etc. can be used as crude acid urease preparation in this invention without any further treatment or after drying by freeze-drying, spray drying, acetone drying, etc. It is also practicable that the said enzyme is solubilized by treatment of the cells by freezing-thawing, grinding, sonication, osmotic shock, lysozyme, surfactant, etc. which are used separately or in combination, and then purified by an appropriate combination of the conventional techniques for purification of enzymes, such as protamine treatment, salting out, treatment with an organic solvent, isoelectric precipitation, electrophoresis, ion exchange chromatography, gel filtration, affinity chromatography, and crystallization, to give crude or purified enzyme preparations with higher specific activity than the viable cells, to be used in the method of this invention.

In the following the method of treatment of alcoholic liquors with acid urease is illustrated.

The form of the enzyme used in the treatment of alcoholic liquors with the enzyme may by the bacterial cells containing the enzyme, or crude or purified acid urease preparations obtained by extraction and purification with conventional techniques, or immobilized preparation obtained by including the enzyme preparation in a natural polymer such as agar and carrageenan or a synthetic polymer such as polyacrylamide and urethane resin, or immobilized preparation obtained by binding to a carrier such as active carbon, ceramic, dextran, agarose and its related substances, and porous glass.

The alcoholic liquors to be treated with the method in this invention are those containing carbamide, including brewages such as refined sake, beer, wine, fruit wines, samshu, whisky mash, shochu mash (Sochu; Japanese spirit), and brandy mash, etc., and the intermediate products thereof. For example, in the case of sake, final mash, unrefined sake in a vat after filtration by compression of the mash, raw sake, preservative sake after pasturization, refined sake before bottling, etc. may be treated with the method of this invention, but treatment with the said enzyme added before pasteurization is most desirable.

When these alcoholic liquors are to be treated with acid urease, it is practically advantageous that acid urease is added at 0.00001 unit/ml to 1 unit/ml, particularly at 0.0001 unit to 0.1 unit/ml. One unit means the amount of the enzyme required to decompose carbamide to release one micromole of ammonia per unit time (minute). One unit is written as 1 U hereinafter.

Temperature of the treatment of alcoholic liquors is usually 0° C. to 80° C., preferably 10° C. to 60° C. The pH is 2 to 7, desirably 3 to 5. The treatment is continued for a time sufficient to remove carbamide in the alcoholic liquors usually for 20 minutes to 200 days, more frequently for 5 hours to 120 days.

The treatment of alcoholic liquors with acid urease can be also carried out by allowing viable cells of acid urease-producing microorganisms to coexist during the processes of alcohol fermentation in the production of alcoholic liquors.

Acid urease-producing bacteria may be added at any time before completion of alcohol fermentation. Preferably acid urease-producing bacteria are inoculated and allowed to grow during the process to produce yeast mash or the process to prepare saccharified mixture, and then subjected to main fermentation (alcohol fermentation) according to the conventional method. Acid urease-producing bacteria may be inoculated and cultured at an appropriate time during the main fermentation, preferably before the middle of the whole fermentation period.

When acid urease-producing bacteria are allowed to grow in the yeast mash of alcoholic liquors, acid urease-producing bacteria are inoculated before usual addition of yeast and yeast is inoculated when the acid urease-producing bacteria have grown sufficiently; then seed mash is prepared according to the conventional method and used for mashing. When acid urease-producing bacteria are allowed to grow in raw materials or saccharified raw materials, acid urease-producing bacteria are inoculated to raw materials [e.g. steamed rice, koji rice (a culture of *Aspergirus oryzae* on steamed rice), malt, barley juice, grape juice, starch] or to saccharified raw materials and used for mashing after sufficient growth.

Cultivation temperature of acid urease-producing bacteria is not specified, though preferably 28°-40° C. The count of grown acid urease-producing bacteria is not specified, though preferably $10^8$/ml or more. Seed mash or raw materials or saccharified raw materials containing grown acid urease-producing bacteria may be used at any mashing stage or at any time of mashing process before completion of alcohol fermentation. For example in production of refined sake they may be used at the time of the first, middle, or stopping addition in mashing process, or at any time during the mashing process. The amount to be added of seed mash or raw materials or saccharified raw materials containing grown acid urease-producing bacteria is not specified but preferably 3–15%.

When acid urease-producing bacteria are to be added to seed mash, addition of an acid is unnecessary if the bacteria are of acid-producing strains, whereas an acid such as lactic acid is added prior to addition of yeast, in an amount almost equivalent to that used usually to seed mash if the bacteria do not produce acid.

Alcohol fermentation in this invention can be conducted under conventional conditions (temperature, time, etc.), and no modification is required in the conditions of subsequent processes such as filtration, compressfiltration, pasteurization, storage, aging, and distillation.

The method of this invention of treatment of alcoholic liquors with acid urease is economically more advantageous because only a much smaller amount of urease is required, as compared with the conventional methods of treatment with neutral to alkaline urease from Canavalia Adans. Namely, the method of this invention requires only about 1/100–1/10000 enzyme unit or about 1/10–1/100 or less weight of that required in the conventional methods for complete removal by decomposition of carbamide. Therefore, deterioration due to residual urease in alcoholic liquors after the treatment is practically negligible, which is a more advantageous point as compared with the conventional methods.

In addition, decomposition of carbamide can proceed at a higher temperature in a short time even at an acidic pH 3–5 common to alcoholic liquors with the method of this invention; carbamide can be decomposed at a high efficiency, which is industrially advantageous.

In the following this invention is illustrated in more concrete with Examples. The Examples are no more than examples and do not limit the scope of the invention at all.

The activity of acid urease in a culture was determined colorimetrically by the nitroprusside method on ammonia produced by the reaction at 37° C. for 30 minutes of the mixture of a volume of a suspension in sterilized deionized water of the cells collected by centrifugation of the culture which had been diluted appropriately, with an equal volume of 0.2M citrate buffer (pH 4.0) containing urea. The activity was expressed in unit; one unit (1 U) means the amount of enzyme to produce one micromole of ammonia per unit time (minute).

EXAMPLE 1

Lactobacillus fermentum JCM 5867 (IFO 14511, FERM BP-1454) grown by stabculture in a medium consisting of 0.5% of glucose, 1.0% of polypeptone, 1.0% yeast extract, 0.5% meat extract, 0.5% of common salt, 1.0% of calcium carbonate, and 1.5% of agar was inoculated into two 200 ml-Erlenmeyer flasks each containing 50 ml of a sterilized medium pH 7.0 (neutralized with 30% caustic soda) consisting of 2.0% of glucose, 2.0% of anhydrous sodium acetate, 1.0% of polypeptone, 1.0% of meat extract, 0.2% of yeast extract, 0.5% of common salt, and 0.005% of manganese sulfate (containing about 4 moles of crystal water per mole), followed by standing culture at 37° C for 24 hours. The resulting seed culture in each flask was transferred into one of two 2 l-Erlenmeyer flasks each containing 1 l of the sterilized medium of the same composition as described above, followed by standing culture at 37° C. for 24 hours. The activity of urease in these cultures was 0.1 U/ml.

The cells were collected from the cultures by centrifugation, washed with 0.05M phosphate buffer (pH 7.2) twice, suspended in a liquid containing 30 ml of 0.05M phosphate buffer (pH 7.2), 0.02M EDTA, and 0.01 M dithiothreitol, and sonicated; the supernatant was subjected to fractionation with ammonium sulfate, and the precipitates obtained with 40% to 70% saturation were collected, which were dissolved in 10 ml of 0.05 M phosphate buffer, dialyzed overnight, and freeze-dried, to give 260.4 mg of crude enzyme powders of acid urease. The urease activity was 0.5 U/mg, and the efficiency of purification was 65.1%

The general properties of the crude enzyme powders are as follows:

| | |
|---|---|
| optimal pH | pH 2–4.5 |
| optimal temperature | 60–70° C. |
| pH stability | stable at pH 2–10 when treated at 37° C. for 2 hours |
| thermostability | stable below 60° C. when treated at pH 4 for 2 hours |

Then the crude enzyme powders were dissolved in refined sake (containing 20% of alcohol and 30 ppm of carbamide, pH 4.3) so that the concentration might be 0.02 U/ml or 0.1 U/ml, and kept at 30° C. to cause decomposition of carbamide in refined sake; the result is shown in Table 1. Commercially available urease preparation from Canavalia Adans. was used at 10 U/ml as the control. Carbamide in refined sake was reduced by only about half when treated with the urease from Canavalia Adans. at 10 U/ml for 5 days, whereas the acid urease at as low as 0.1 U/ml decomposed completely the carbamide only in one day.

Activity of acid urease and that of urease from Canavalia Adans. were determined by colorimetry with the nitroprusside method on ammonia produced at pH 4.0 and pH 7.0, respectively. Content of carbamide in refined sake was determined by the enzymatic method using NADP+dependent glutamate dehydrogenase on ammonia produced by decomposition of carbamide with urease.

These methods of determination were applied also in the following Examples.

TABLE 1

| kind and amount of urease used | days of treatment | | | |
|---|---|---|---|---|
| | 0 day | 1 day | 2 days | 5 days |
| acid urease 0.02 U/ml | ppm 30 | ppm 5 | ppm 3 | ppm 0 |
| acid urease 0.1 U/ml | 30 | 0 | 0 | 0 |
| urease from Canavalia Adans. 10.0 U/ml | 30 | 18 | 14 | 13 |

EXAMPLE 2

To raw sake (containing 20% of alcohol and 30 ppm of carbamide, pH 4.3) were added the crude enzyme powders of acid urease obtained in Example 1 so that the activity of acid ruease might be 0.01 U/ml or 0.003 U/ml, and kept at 10° C. or at 15° C. to decompose carbamide. As shown in Table 2, carbamide in raw sake was decomposed completely after treatment with acid urease at 0.003 U/ml at 10° C. for 8 days. A sensory test showed that the refined sake obtained after the treatment was qualitatively more desirable with less off-flavor than the control refined sake (not treated with the crude enzyme powders of acid urease).

TABLE 2

| temperature | amount of urease | days of treatment | | | | |
|---|---|---|---|---|---|---|
| | | 0 | 2 | 4 | 6 | 8 |
| | mU/ml | ppm | ppm | ppm | ppm | ppm |
| 10° C. | 10 | 30 | 12 | 4 | 0 | 0 |
| | 3 | 30 | 18 | 10 | 4 | 0 |
| 15° C. | 10 | 30 | 8 | 0 | 0 | 0 |
| | 3 | 30 | 14 | 8 | 3 | 3 |

EXAMPLE 3

Cells were collected from 4 l of the culture of Lactobacillus fermentum JCM 5867 (IFO 14511, FERM BP-1454) obtained by culture in the same way as in Example 1, and freeze-dried to give 2.0 g of dried cells. The activity of acid urease of these dried cells was 0.35 U/mg.

Raw sake (containing 20% of alcohol and 30 ppm of carbamide, pH 4.3) was pasteurized at 75° C. for 1 minute and cooled rapidly to 30° C., to which the dried cells described above were added so that the activity of acid urease might be 0.01 U/ml or 0.003 U/ml, and kept at 30° C. Change of the concentration of carbamide along time is shown in Table 3.

TABLE 3

| amount of urease | days of treatment | | | |
|---|---|---|---|---|
| | 0 | 4 | 6 | 10 |
| 10 mU/ml | 30 ppm | 9 ppm | 0 ppm | 0 ppm |
| 3 | 30 | 16 | 7 | 0 |

EXAMPLE 4

Refined sake (containing 20% of alcohol and 30 ppm of carbamide, pH 4.3) was pasteurized at 62° C. for 15 minutes and cooled rapidly to 55° C., when the crude enzyme powders of acid urease obained in Example 1 were added and dissolved aseptically so that the activity might be 0.003 U/ml, cooled rapidly to room temperature, and stored under conventional condition for refined sake. Change of concentration of carbamide along time is shown in Table 4.

TABLE 4

| amount of urease | days of treatment | | | |
|---|---|---|---|---|
| | 0 | 4 | 7 | 10 |
| 3 mU/ml | 30 ppm | 12 ppm | 4 ppm | 0 ppm |
| temperature of the mixture | 20° C. | 21° C. | 23° C. | 24° C. |

EXAMPLE 5

To the final mash of sake after completion of fermentation (containing 18% of alcohol and 30 ppm of carbamide, pH 4.2) were added the crude enzyme powders of acid urease obtained in Example 1 so that the activity might be 0.01 U/ml, kept at 13° C., and filtrated into vats three days later. Carbamide in the final mash was decomposed completely in 3 days as shown in Table 5. Neither carbamide was detected in sake in the vats after filtration of the final mash.

TABLE 5

| | days of treatment | | | | |
|---|---|---|---|---|---|
| | 0 | 1 | 2 | 3 | sake in vats |
| carbamide (ppm) | 30 | 18 | 8 | 0 | 0 |

EXAMPLE 6

In beer (containing 4.2% of alcohol and 5.1 ppm of carbamide, pH 4.2) were dissolved the crude enzyme powders of acid urease obtained in Example 1 so that the concentration might be 0.003 U/ml, and kept at 10° C. for 3 days; change of the concentration of carbamide in beer is shown in Table 6. Carbamide could be decomposed completely in 3 days. A sensory test showed that the beer thus treated was better with less off-flavor than beer without treatment with acid urease.

TABLE 6

| | day of treatment | | | |
|---|---|---|---|---|
| | 0 | 1 | 2 | 3 |
| carbamide (ppm) | 5.1 | 3.0 | 1.5 | 0 |

EXAMPLE 7

Cells were collected by centrifugation from 4 l of culture of Lactobacillus fermentum JCM 5867 (IFO 14511, FERM BP-1454) obtained in the same way as described in Example 1, and freeze-dried to give 2.0 g of dried cells. The activity of acid urease in these dried cells was 0.35 U/mg. These dried cells were suspended in refined sake (containing 20% of alcohol and 30 ppm of carbamide, pH 4.3) at the concentration of 0.5 mg/ml, and kept at 50° C. for 6 hours, so that carbamide disappeared completely.

EXAMPLE 8

To wine (containing 12.1% of alcohol and 6.2 ppm of carbamide, pH 3.7) were added dried cells containing acid urease obtained in Example 7 so that the activity might be 0.03 U/ml, and kept at 15° C. for 5 days, so that carbamide in wine disappeared completely.

Then the cells were removed from the wine and compared with wine without treatment with the cells in a sensory test; the wine treated with the cells was better with less off-flavor.

EXAMPLE 9

To whisky mash (containing 5.3% of alcohol and 5.0 ppm of carbamide, pH 4.3) were added the crude enzyme powders of acid urease obtained in Example 1 at the concentration of 0.01 U/ml, and kept at 22° C. for 24 hours, so that carbamide in the whisky mash was decomposed completely.

The whisky mash thus treated and a whisky mash without such treatment were distilled twice each in glass distillator, to give whisky products containing 50% of alcohol. These two products were compared in a sensory test; the whisky product after the treatment was better with less off-flavor.

EXAMPLE 10

To rice shochu mash (containing 17.5% of alcohol and 30 ppm of carbamide, pH 3.8) were added dried cells containing acid urease obtained in Example 7 so that the activity might be 0.03 U/ml, and kept at 15° C.

for 2 days, so that carbamide in the shochu mash disappeared completely.

The shochu mash with the cells added and that without the cells were distilled under reduced pressure, to give shochu products containing 40% of alcohol. These two products were compared in a sensory test; the product obtained after the treatment was better with less off-flavor.

EXAMPLE 11

*Lactobacillus fermentum* JCM 5867 (IFO 14511, FERM BP-1454) grown by stab culture in a medium consisting of 0.5% of glucose, 1.0% of polypeptone, 1.0% of yeast extract, 0.5% of meat extract, 0.5% of common salt, 1.0% of calcium carbonate, and 1.5% of agar was inoculated into two 1 l-Erlenmeyer flasks each containing 500 ml of a sterilized medium pH 7.0 (neutralized with 30% caustic soda) consisting of 2.0% of glucose, 2.0% of anhydrous sodium acetate, 1.0% of polypeptone, 1.0% of meat extract, 0.2% of yeast extract, 0.5% of common salt, and 0.005% of manganese sulfate (containing about 4 moles of crystal water per mole), followed by standing culture at 37° C. for 24 hours, so that the viable count became $2.4 \times 10^8$/ml. The resulting seed culture was centrifuged at 10000 rpm for 10 minutes, and the collected cells were washed with 500 ml of sterilized water and centrifuged again. The washed cells were suspended in 10 ml of sterilized water.

To the mixture of steamed rice and koji corresponding to 30 kg of well-milled rice and 30 kg of koji rice was added 120 of water and saccharified by keeping at 55° C. for 5 hours. The saccharified mixture was sterilized by warming to 70° C. and keeping at the temperature for 5 minutes, and then cooled to 35° C. To this was added 10 ml of the viable cell suspension of *Lactobacillus fermentum* JCM 5867 described above. Then the mixture was incubated at 35° C. for 2 days. The count of the lactic acid bacteria was controlled to be $2 \times 10^8$/ml. The mixture was cooled at 28° C., to which sake yeast kyokai-7 was inoculated so that the concentration might be $2 \times 10^7$/ml; the mash was given the first addition after 4 days of incubation, allowed to set with no addition (odori) for one day, and then given the second addition and the third addition; then fermentation is allowed to proceed under conventional temperature change. Then on the 19th day the mash was given the fourth addition and alcohol and the unrefined sake was filtrated into vats. The quantities of ingredients at each stage of mashing in this Example are listed in Table 7. The changes in seed mash are summarized in Table 8. The result of analysis of the sake filtrated into vats is shown in Table 9. As shown clearly in the Tables, carbamide was hardly detected because it had been decomposed by acid urease in the final mash prepared from the seed mash treated with the acid urease-producing lactic acid bacteria whereas it was detected in the control. The quality of the product was also better with richer taste than the control.

TABLE 7

| | Quantities of ingredients at each stage of mashing process (kg) | | | | | |
|---|---|---|---|---|---|---|
| | sake yeast culture | first addn. | second addn. | third addn. | 4th addn. | total |
| whole rice | 60 | 130 | 255 | 475 | 80 | 1000 |
| steamed rice | 30 | 95 | 200 | 395 | 80 | 800 |
| koji rice | 30 | 35 | 55 | 80 | | 200 |
| water | 120 | 100 | 320 | 620 | 150 | 1310 |

TABLE 8

| Changes in seed mash along time | | | | | | |
|---|---|---|---|---|---|---|
| days after yeast addition | | 1 | 2 | 3 | 4 | 5 |
| Baum (Be') | control | 11.3 | 10.1 | 8.9 | 7.7 | 6.1 |
| | this invention | 13.5 | 10.5 | 7.8 | 6.6 | 6.0 |
| alcohol (Alc.) | (%) control | | 1.5 | 3.6 | 5.8 | 7.0 |
| | this invention | | 1.5 | 5.0 | 6.3 | 6.7 |
| acidity (T.A) | control | 4.10 | 5.10 | 5.75 | 6.32 | 7.10 |
| | this invention | 5.58 | 8.28 | 10.18 | 9.85 | 9.90 |
| amino acid acidity (A.A) | control | 2.0 | 1.71 | 1.85 | 1.80 | 1.90 |
| | this invention | 5.30 | 4.57 | 3.77 | 3.60 | 3.45 |
| *Lactobacillus fermentum* JCM 5867 count ($\times 10^6$) | control | 0.0 | 0.0 | 0.0 | 0.0 | 0.0 |
| | this invention | 380 | 400 | 400 | 400 | 400 |
| lactic acid (ppm) | control | 510 | 615 | 700 | 810 | 920 |
| | this invention | 1094 | 1157 | 1230 | 1270 | 1260 |

TABLE 9

| Result of analysis of sake filtrated into vats | | | | | |
|---|---|---|---|---|---|
| | Be' | Alc. | T.A | A.A | carbamide (ppm) |
| control | −2.3 | 19.9 | 1.80 | 1.75 | 15.3 |
| this invention | −2.0 | 19.9 | 1.85 | 1.82 | 0.0 |

EXAMPLE 12

To the mixture of steamed rice and koji corresponding to 60 kg of well-milled rice and 40 kg of koji rice was added 180 l of water and saccharified by keeping at 55° C. for 5 hours. The saccharified mixture was pasteurized by warming to 70° C. and keeping at the temperature for 5 minutes, and then cooled to 35° C. To this cooled saccharified mixture was added 40 ml of the viable cell suspension of *Lactobacillus fermentum* JCK 5867 obtained as described in Example 11. Then the mixture was incubated at 35° C. for 2 days. The count of the lactic acid bacteria was controlled to be $2 \times 10^8$/ml. The whole amount of this saccharified mixture (4th addition) was added to the mash on the 12th day and 5th addition and alchol were added on the 18th day and the sake was filtrated into vats. The quantities of ingredients at each stage of mashing in this Example are listed in Table 10, and change of carbamide content in the mash along time is shown in Table 11. The latter Table indicates that carbamide content in the mash to which the 4th addition treated with acid urease-producing lactic acid bacteria (4th addition) had been added decreased after the addition and became 0 at the time of filtration into vats, suggesting that carbamide had been decomposed by acid urease. Neither in the sake in vats was detected carbamide. A sensory test showed that the quality of the sake in vats was excellent with rich and refreshing taste.

TABLE 10

Quantities of ingredients at each stage of mashing process (kg)

| | sake yeast culture | first addn. | second addn. | third addn. | 4th addn. | 5th addn. | total |
|---|---|---|---|---|---|---|---|
| whole rice | 50 | 125 | 235 | 430 | 100 | 60 | 1000 |
| koji rice | 25 | 35 | 45 | 60 | 40 | | 205 |
| steamed rice | 25 | 90 | 190 | 370 | 60 | 60 | 795 |
| water | 100 | 100 | 290 | 550 | 180 | 120 | 1340 |

TABLE 11

Change of carbamide content in mash (ppm)

| age of mash (days) | 12 | 13 | 14 | 16 | 18 | sake in vats |
|---|---|---|---|---|---|---|
| control | 21 | 24 | 26 | 28 | 30 | 24 |
| this invention | 21 | 11 | 3 | 1.2 | 0 | 0 |

EXAMPLE 13

*Streptococcus mitior* PG-154 (IFO 14633, FERM BP-1448) grown on a commercial GAM semisolid medium (Nissui Seiyaku Co., Japan) was inoculated to a 200 ml-Erlenmeyer flask containing 50 ml of a sterilized seed medium pH 7.0 (neutralized with 30% caustic alkali) consisting of 3% of glucose, 1.5% of polypeptone, 1% of meat extract, 0.8% of yeast extract, 0.5% of common salt, 0.2% of anhydrous sodium acetate, 0.005% of manganese sulfate (containing about 4 moles of crystal water per mole), and 0.001% of cobalt sulfate (heptahydrate), and subjected to standing culture at 34° C. for 24 hours. Five ml of this seed culture was transferred into a 200 ml-Erlenmeyer flask containing 100 ml of a sterilized medium of the same composition and subjected to standing culture at 32° C. for 2 days. The activity of acid urease of this culture was determined and the potency was 0.6 U/ml.

Five ml of the culture obtained as described above was centrifuged at 3000 rpm for 10 minutes to collect the cells. The cells were then washed with water, centrifuged, and suspended in 1 ml of sterilized water, to which 50 μl of isobutanol was added and kept at 50° C. for 15 minutes, to give an enzyme solution of which optimal pH was determined by using 0.2M citrate buffer. The result is shown in Table 12. As shown in the Table, all of the strains in this invention had strong urea-decomposing activities in the acidic region.

TABLE 12

| pH | 3 | 4 | 5 | 6 | 7 | 8 | 9 |
|---|---|---|---|---|---|---|---|
| relative activity (%) | 68 | 100 | 98 | 67 | 26 | 14 | 13 |

Cells were collected from 80 ml of the culture by centrifugation, sterilized by immersing in 50% ethanol, centrifuged and freeze-dried. The resulting dried cells weighed 16.9 mg with acid urease activity of 1.44 U/mg.

The dried cells were added to refined sake (containing 20% of alcohol and 30 ppm of carbamide, pH 4.3) so that the acid urease activity might be 0.01 U/ml, and kept at 30° C. to decompose carbamide in refined sake; the result is shown in Table 13.

TABLE 13

| days of treatment | 0 | 2 | 4 | 6 | 10 |
|---|---|---|---|---|---|
| carbamide (ppm) | 30 | 11 | 2 | 0 | 0 |

EXAMPLE 14

The strains listed in the following Table 14 grown in commercial GAM semisolid media (Nissui Seiyaku Co., Japan) were inoculated to 200 ml-Erlenmeyer flasks each containing 50 ml of sterilized commercial GAM broth (Nissui Seiyaku Co., Japan), and subjected to standing culture at 34° C. for 24 hours. Five ml each of the seed culture thus obtained was transferred into 200 ml-Erlemeyer flasks each containing 100 ml of a sterilized medium obtained by addition of 0.005% of manganese sulfate (containing about 4 moles of crystal water per mole) to the same commercial GAM broth, and subjected to standing culture at 32° C. for 3 days. The acid urease activities of these cultures were determined, and the result is shown in Table 14.

TABLE 14

| Strain | acid urease activity in culture (U/ml) |
|---|---|
| *Streptococcus bovis* PG-186 (IFO 14634, FERM BP-1449) | 0.4 |
| *Bifidobacterium choerinum* PG-196 (IFO 14635, FERM BP-1450) | 1.2 |

Cells were collected by centrifugation at 3000 rpm for 10 minutes from 5 ml of the culture obtained by the method described above, washed with water, centrifuged, and suspended in 1 ml of sterilized water, to which 50 μl of isobutanol was added and kept at 50° C. for 15 minutes; the resultant enzyme solution was studied with respect to its optimal pH by using 0.2M citrate buffer. The result is shown in Table 15. As shown in the Table, the strains in this invention showed strong urea-decomposing activities in the acidic region.

Cells were collected by centrifugation from 80 ml each of cultures of PG-186 and PG-196 strains obtained by the method described above, sterilized by immersing in 50% ethanol for 4 hours, centrifuged and freeze-dried. The dried cells thus obtained weighed 30.2 mg and 64.0 mg, with acid urease activity of 0.38 U/mg and 0.6 U/mg, respectively.

The dried cells were added to refined sake (containing 20% of alcohol and 30 ppm of carbamide, pH 4.3) so that the acid urease activity might be 0.01 U/ml, kept at 30° C. to decompose carbamide in refined sake. The result is shown in Table 16.

TABLE 15

| | relative activity (%) | |
|---|---|---|
| pH | PG-186 | PG-196 |
| 3 | 40 | 35 |
| 4 | 85 | 100 |
| 5 | 100 | 30 |
| 6 | 70 | 35 |
| 7 | 35 | 23 |
| 8 | 17 | 38 |
| 9 | 15 | 35 |

TABLE 16

| | days of treatment | | | | |
|---|---|---|---|---|---|
| urease derived from | 0 | 2 | 4 | 6 | 10 |
| PG-186 | 30 | 10 | 0 | 0 | 0 |

TABLE 16-continued

| urease derived from | days of treatment | | | | |
|---|---|---|---|---|---|
| | 0 | 2 | 4 | 6 | 10 |
| PG-196 | 30 | 18 | 8 | 1 | 0 |

EXAMPLE 15

*Lactobacillus fermentum* JCM 5867 (IFO 14511, FERM BP-1454) was inoculated into ten 200 ml-Erlenmeyer flaskes each containing 50 ml of a sterilized seed medium pH 7.0 (neutralized with 30% caustic soda) consisting of 3% of glucose, 1.5% of polypeptone, 1% of meat extract, 0.8% of yeast extract, 0.5% of common salt, 0.2% of anhydrous sodium acetate, 0.005% of manganese sulfate (containnning about 4 moles of crystal water per mole) and 0.001% of nickel sulfate (hexahydrate), followed by standing culture at 34° C. for 24 hours. The resulting seed culture in each flask was transferred into ten 2 l-Erlenmeyer flasks each containing 1 l of the sterilized medium pH 7.0 (neutralized with 30% caustic soda) consisting of 4% of glucose, 1.5% of polypeptone, 1% of meat extract, 0.8% of yeast extract, 0.5% of common salt, 0.2% of anhydrous sodium acetate, 0.5% of urea, 0.05% of manganese sulfate (containing about 4 moles of crystal water per mole), 0.002% of nickel sulfate (hexahydrate), 0.002% of cobalt sulfate and 0.001% of strontium sulfate, followed by standing culture at 32° C. for 2 days to give 10 l of the culture having acid urease activity of 5.6 U/ml. The cells were collected from the cultures by centrifugation, suspended in water, and spray-dried to give dried cells having the activity of acid urease. By repeating the method described above, 1.8 kg of the crude enzyme was obtained from 1000 l of the culture. The activity of crude acid urease powder was 2600 U/g. The resulting crude enzyme powder (1.15 Kg) and 30 kg of short fibers of wood pulp (a filter aide, trade name "KC Flock ® W-200", Takeda Chemical Industries, Ltd., Japan) were mixed by using a micro-speed mixer (Takara Kouki Co., Japan) at 500 r.p.m. for 2 minutes to give about 31 kg (water content: 3%) of the enzyme composition having the urease activity of 96 U/g. A portion (0.1 g) of the resulted composition was added to 1 l of refined sake (containing 16% of alcohol and 50 ppm of carbamide, pH 4.4), stored at 30° C. for 10 days and filtered. No residual carbamide was detected in the filtered sake.

REFERENCE EXAMPLE 1

*Lactobacillus reuteri* Rt-5 (IFO 14631, FERM BP-1477) grown on a commercial GAM semisolid medium (Nissui Seiyaku co., Japan) was inoculated to ten 200 ml-Erlenmeyer flasks containing 50 ml of a sterilized seed medium pH 7.0 (neutralized with 30% caustic alkali) consisting of 3% of glucose, 1.5% of polypeptone, 1% of meat extract, 0.8% of yeast extract, 0.5% of common salt, 0.2% of anhydrous sodium acetate, 0.005% of manganese sulfate (containing about 4 moles of crystal water per mole), and 0.001% of nickel sulfate (hexahydrate), and subjected to standing cultgure at 34° C. for 24 hours. This seed culture was transferred into ten 2 l-Erlenmeyer flasks containing 1 l of a sterilized medium of the same composition as described above and subjected to standing culture at 32° C. for 2 days to givce 10 l of the culture having the acid urease activity of 21.6 U/ml. The cells were collected from the cultures by centrifugation, washed with 0.05M phosphate buffer (pH 7.2) twice, suspended in 4 l of a solution containing 1 mM EDTA and 1mM dithiothreitol, broken down by treating with a cell mill containing 2 l of glass beads (0.1 to 0.2 mm in diameter) at 4500 rpm for 20 minutes. The treated product was centrifuged and to the supernatant was added ethanol so that the concentration comes to be 80%. The precipitate was collected by centrifugation, dissolved in 0.05M torishydrochloric acid buffer (pH 7.0) containing 1 mM of EDTA and 2-mercapto ethanol, adsorbed on a sephadex-G 100 column (7.5 cm in diameter and 90 cm in length), and eluted with the same buffer solution as described above to collect the active fractions. The collected fraction was passed through a sephadex G-200 column (4.5 cm in diameter, 150 cm in length) bufferized with the above-mentioned buffer solution, eluted with the buffer solution to collect the active fractions, passed through a DEAE sephadex CL-6B column, and subjected to gradient elution using buffer solution containing 0–0.7M sodium chloride to collect the active fractions. The obtained solution was concentrated by using a ultra filter, Amicon 8200 Model, UK-50 film (fractionating at molecular weight of 50,000), and the buffer solution was exchanged to 0.005M phosphate buffer (pH 7.0) containing 1 mM 2-mercapto ethanol. The treated solution was passed through a affinity gel chromatogram column (4 cm in diameter and 50 cm in length) prepared from AFFI-PREP[10] (bead-carrier made from a polymer belonging to polymetaacrylates, Bio-Rad Co., U.S.A.) and hydroxyurea, subjected to gradient elution using 0.005M to 0.044M phosphate buffer to collect the active fractions, concentrated by the ultra filter identified above, desalted, and lyophilized to give powder (104 mg) of purified enzyme. The powder possessed the specific activity of 336.5 U/mg, and showed single protein band in the electrophoresis using polyacryl amide. These passage of purification was shown the following Table.

| Purification Process | Total protein (g) | Total activity ($\times 10^3$U) | Specific activity (U/mg) | Yield (%) |
|---|---|---|---|---|
| Cell-free extract | 14.1 | 183.3 | 13.0 | 100.0 |
| Ethanol | 5.2 | 157.6 | 30.3 | 86.0 |
| Sephadex G-100 | 3.0 | 140.1 | 46.7 | 76.4 |
| Sephadex G-200 | 1.0 | 78.7 | 78.7 | 42.9 |
| DEAE Cephalose CL-6B | 0.37 | 60.7 | 164.0 | 33.1 |
| Affinity gel | 0.10 | 35.4 | 354.0 | 19.3 |
| Lyophilized | 0.10 | 35.0 | 336.5 | 19.1 |

The enzymological and physicochemical properties of the lyophilized product obtained by the above-mentioned method are as follows:

(1) Action

This produces 2 moles of ammonia and 1 mole of carbon dioxide gas from 1 mole of urea and 1 mole of water.

(2) Substrate specificity

This acts on urea most suitably and ethylurea, biuret, allantoic acid and allantoin to some extent (the following Table).

| Substrate | Relative activity (%) |
|---|---|
| Urea | 100.0 |
| Allantoin | 1.2 |
| Allantoic acid | 8.8 |
| Biuret | 64.1 |
| Methylurea | 4.9 |
| Ethylurea | 41.1 |

(3) Optimal pH and pH stability

Optimal at pH 2 to 4.5, stable at pH 6 to 7 and considerably stable at pH 2 to 10 when treated at 37° C. for 30 minutes.

(4) Optimal pH and thermostability

Optimal at 60° C. to 70° C., stable to 60° C. at pH 4.

(5) Inhibitors

The enzyme action is inhibited by mercuric chloride, silver nitrate or iodoacetic acid.

| Inhibitor | Concentration | Relative activity (%) |
|---|---|---|
| none | | 100.0 |
| Ag NO$_3$ | 0.05 mM | 0.7 |
| Hg Cl$_2$ | 0.05 mM | 0.6 |
| Iodoacetic acid | 1 mM | 15.4 |

(6) Molecular weight

About 220,000 according to sephadex G-200 gel filtration.

(7) Isoelectric point

About 4.7 according to isoelectrophoresis using acryl-amide.

(8) Structure of crystal

This enzyme is difficult to crystalize.

(9) Elementary analysis

The measurement was not carried out because the crystalization is difficult.

(10) Km value

The Km value is $1.7 \times 10^3$M (pH 4, citrate buffer).

What is claimed is:

1. A method for improving the quality of alcoholic liquors, which comprises adding an acid urease, which produces 2 moles of ammonia and 1 mole of carbon dioxide gas from 1 mole of carbamide and 1 mole of water and has an optimal pH for decomposing said carbamide in the acidic region, at an amount of 0.0001 to 1 unit/ml to alcoholic liquors containing carbamide and decomposing said carbamide.

2. The method according to claim 1, wherein the alcoholic liquor is a brewage selected from the group consisting of sake, beer, wine, fruit wine, samshu, whisky mash, shochu mash and brandy mash.

3. The method according to claim 1, wherein the acidic region is 2 to 5.

4. A method of improving the quality of alcoholic liquors, which comprises adding a sufficient amount of viable cells of acid urease-producing microorganisms of *Lactobacillus fermentum, Streptococcus mitior, Streptococcus bovis* or *Bifidobacterium choerinum* to a fermentation reaction mixture in a process for the procution of alcoholic liquors by fermentation, wherein said said alcoholic liquids contain carbamide and wherein said amount of cells is sufficient to reduce the amount of said carbamide.

5. The method according to claim 4, wherein said cells are inoculated and cultured in a process for the production of alcoholic liquors before completion of the alcohol fermentation.

* * * * *